(12) United States Patent
Leclere

(10) Patent No.: US 12,403,236 B2
(45) Date of Patent: Sep. 2, 2025

(54) MODULAR, MULTI-SPECIALTY FLUID PUMP

(71) Applicant: Stryker Corporation, Kalamazoo, MI (US)

(72) Inventor: Theodore Leclere, San Francisco, CA (US)

(73) Assignee: Stryker Corporation, Portage, MI (US)

( * ) Notice: Subject to any disclaimer, the term of this patent is extended or adjusted under 35 U.S.C. 154(b) by 172 days.

(21) Appl. No.: 17/335,594

(22) Filed: Jun. 1, 2021

(65) Prior Publication Data

US 2021/0369940 A1     Dec. 2, 2021

Related U.S. Application Data

(60) Provisional application No. 63/033,761, filed on Jun. 2, 2020.

(51) Int. Cl.
*A61M 1/00* (2006.01)
*F04B 43/12* (2006.01)
*F04D 1/00* (2006.01)

(52) U.S. Cl.
CPC ............ *A61M 1/77* (2021.05); *A61M 1/72* (2021.05); *F04B 43/1253* (2013.01); *F04D 1/00* (2013.01); *A61M 2205/6054* (2013.01)

(58) Field of Classification Search
CPC ........ A61M 1/72; A61M 1/77; A61M 3/0201; A61M 2205/6054; A61M 2205/121; A61M 1/3622; A61M 1/36222; A61M 1/362227; A61M 1/36225; F04D 1/00; F04D 7/00; F04D 17/00; F04B 43/1253
See application file for complete search history.

(56) References Cited

U.S. PATENT DOCUMENTS

| | | | |
|---|---|---|---|
| 5,133,650 A | 7/1992 | Sunderland et al. | |
| 5,246,422 A | 9/1993 | Favre | |
| 5,460,490 A * | 10/1995 | Carr .................... | A61M 1/7415 417/474 |
| 5,464,391 A | 11/1995 | Devale | |
| 5,484,402 A | 1/1996 | Saravia et al. | |
| 5,620,312 A | 4/1997 | Hyman et al. | |
| 5,655,897 A * | 8/1997 | Neftel .................... | F04B 43/12 417/477.2 |
| 6,077,246 A | 6/2000 | Kullas et al. | |

(Continued)

FOREIGN PATENT DOCUMENTS

WO     2019/094927 A1     5/2019

OTHER PUBLICATIONS

Radgowski et al., Restriction Requirement dated Dec. 24, 2009, directed to U.S. Appl. No. 11/639,360; 6 pages.

(Continued)

*Primary Examiner* — Adam Marcetich
*Assistant Examiner* — Timothy L Flynn
(74) *Attorney, Agent, or Firm* — Morrison & Foerster LLP

(57) ABSTRACT

The present disclosure is directed to a modular, multi-specialty pump system. The pump system includes a pump console with a motor and a sensor and a removable pump cassette attached to the pump console. The pump cassette includes a cassette identifier and the sensor can detect the cassette identifier and adjust at least one operating parameter of the motor depending on the detected cassette identifier of the pump cassette.

26 Claims, 8 Drawing Sheets

(56) References Cited

U.S. PATENT DOCUMENTS

| | | | |
|---|---|---|---|
| 6,110,103 A | 8/2000 | Donofrio | |
| 6,126,592 A | 10/2000 | Proch et al. | |
| 6,162,194 A | 12/2000 | Shipp | |
| 6,213,970 B1 | 4/2001 | Nelson et al. | |
| 6,358,224 B1 | 3/2002 | Tims et al. | |
| 6,436,072 B1 | 8/2002 | Kullas et al. | |
| 6,447,446 B1 | 9/2002 | Smith | |
| 6,623,445 B1 | 9/2003 | Nelson et al. | |
| 6,652,488 B1 | 11/2003 | Cover et al. | |
| 8,052,644 B2 | 11/2011 | Radgowski et al. | |
| 9,700,457 B2 | 7/2017 | Gerg | |
| 2005/0095155 A1 | 5/2005 | Blight et al. | |
| 2006/0073048 A1* | 4/2006 | Malackowski | A61M 3/0208 417/474 |
| 2006/0285986 A1 | 12/2006 | Radgowski et al. | |
| 2007/0078370 A1* | 4/2007 | Shener | A61M 3/0258 604/8 |
| 2007/0233003 A1* | 10/2007 | Radgowski | A61M 1/77 604/151 |
| 2007/0244435 A1* | 10/2007 | Hicks | A61M 5/16804 604/131 |
| 2008/0154182 A1 | 6/2008 | Martin | |
| 2014/0178215 A1 | 6/2014 | Baxter | |
| 2020/0164141 A1* | 5/2020 | Biermann | A61M 5/1413 |
| 2020/0297910 A1* | 9/2020 | Paden | A61M 1/155 |

OTHER PUBLICATIONS

Radgowski et al., US Office Action dated Apr. 27, 2011, directed to U.S. Appl. No. 11/639,360; 10 pages.

Radgowski et al., Notice of Allowance mailed on Sep. 2, 2011, directed to U.S. Appl. No. 11/639,360; 8 pages.

International Preliminary Report on Patentability dated Dec. 6, 2022, directed to International Application No. PCT/US2021/035281; 6 pages.

International Search Report and Written Opinion mailed Sep. 21, 2021, directed to International Application No. PCT/US2021/035281; 9 pages.

* cited by examiner

MODULAR, MULTI-SPECIALTY FLUID PUMP

CROSS-REFERENCE TO RELATED APPLICATIONS

This application claims the priority of U.S. Provisional Application No. 63/033,761, filed Jun. 2, 2020, the entire contents of which are incorporated herein by reference.

FIELD

This disclosure relates to a fluid pump system. More particularly, this disclosure relates to a fluid pump system that includes a pump console comprising a motor and a sensor and a pump cassette comprising a cassette identifier, wherein the sensor detects the cassette identifier and the pump console can adjust at least one operating parameter of the motor depending on the detected cassette identifier of the pump cassette.

BACKGROUND

Various fluid pump systems exist for surgical operations. One example of such a pump system is the Stryker AHTO pump for laparoscopic irrigation. The AHTO pump system is a wireless system that includes a cordless irrigation console. The console offers interactive flow rates and battery level displays that enable easy set up and fast operating room turnover times. Cassette tube sets can be inserted into the console for instant activation of the pump system. However, there are many different types of pump specialties besides laparoscopic irrigation.

SUMMARY

Applicant has discovered a multi-specialty pump system that can vary the categorical type of pump mechanism based on the pump cassette that is attached to the pump console. The system can include a universal pump console that can accept removable pump cassettes with tube sets designed for various specialties (e.g., laparoscopic irrigation, endoscope cleaning, etc.). As such, the pump cassette that is attached to the pump console determines the categorical type of fluid pump mechanism, not the pump console. By having a modular pump system like this, a medical facility can consolidate the amount of fluid pump consoles in an operating room while still having an appropriate fluid solution for various specialties.

In typical operating rooms, various pumps are used for various specialties. For example, there can be one pump for laparoscopic suction/irrigation and another pump for intraoperative endoscope cleaning. However, there is currently no system that can combine these two and other very different specialties into one pump system. In Applicant's multi-specialty pump system, the same motor of the pump console can be used for the various different pump cassettes that are attached to the pump console.

In some embodiments, a fluid pump includes a pump console comprising a motor and a sensor; and a pump cassette connected to the pump console comprising a cassette identifier, a fluid inlet, and a fluid outlet, wherein the sensor detects the cassette identifier and the pump console adjusts at least one operating parameter of the motor depending on the detected cassette identifier of the pump cassette. In some embodiments, the sensor is a Hall Effect sensor and the cassette identifier is a magnet. In some embodiments, the sensor is an RFID sensor and the cassette identifier is an RFID tag. In some embodiments, the pump cassette is a centrifugal pump cassette comprising an impeller. In some embodiments, the pump cassette is a peristaltic pump cassette comprising a plurality of rollers. In some embodiments, the at least one operating parameter comprises motor speed, motor direction, and timing. In some embodiments, the pump console comprises a display and the display is adjusted depending on the detected cassette identifier of the pump cassette. In some embodiments, the pump console comprises a motor coupler fixed to a motor shaft of the motor. In some embodiments, the pump cassette comprises a cassette coupler fixed to a first end of a cassette shaft and the motor coupler and the cassette coupler mate together such that the motor drives the cassette shaft of the pump cassette. In some embodiments, the pump cassette comprises an impeller fixed to a second end of the cassette shaft. In some embodiments, the pump cassette comprises a plurality of rollers squeezed between a second end of a cassette shaft and flexible tubing in the pump cassette. In some embodiments, the pump console comprises at least one electrically conductive contact. In some embodiments, the pump cassette comprises at least one flexible electrical contact, wherein the at least one electrically conductive contact of the pump console is in contact with the at least one flexible electrical contact of the pump cassette.

In some embodiments, a pump console includes a motor and a sensor, wherein the pump console is configured to: receive a pump cassette comprising a cassette identifier; detect the cassette identifier of the pump cassette using the sensor; and adjust at least one operating parameter of the motor depending on the detected cassette identifier of the pump cassette. In some embodiments, the sensor is a Hall Effect sensor and the cassette identifier is a magnet. In some embodiments, the sensor is an RFID sensor and the cassette identifier is an RFID tag. In some embodiments, the pump cassette is a centrifugal pump cassette comprising an impeller. In some embodiments, the pump cassette is a peristaltic pump cassette comprising a plurality of rollers. In some embodiments, the at least one operating parameter comprises motor speed, motor direction, and timing. In some embodiments, the pump console includes a display and the display is adjusted depending on the detected cassette identifier of the pump cassette. In some embodiments, the pump console includes a motor coupler fixed to a motor shaft of the motor. In some embodiments, the pump cassette comprises a cassette coupler fixed to a first end of a cassette shaft and the motor coupler and the cassette coupler mate together when the pump console receives the pump cassette such that the motor drives the cassette shaft of the pump cassette. In some embodiments, the pump cassette comprises an impeller fixed to a second end of the cassette shaft. In some embodiments, the pump cassette comprises a plurality of rollers squeezed between a second end of a cassette shaft and flexible tubing in the pump cassette. In some embodiments, the pump console includes at least one electrically conductive contact. In some embodiments, the pump cassette comprises at least one flexible electrical contact, wherein the at least one electrically conductive contact of the pump console is in contact with the at least one flexible electrical contact of the pump cassette when the pump console receives the pump cassette.

In some embodiments, a surgical fluid pump system includes a pump console comprising a motor and a sensor; a pump cassette connected to the pump console comprising a cassette identifier, a fluid inlet, and a fluid outlet; a fluid source fluidly connected to the fluid inlet; and a surgical instrument fluidly connected to the fluid outlet, wherein the sensor detects the cassette identifier and the pump console adjusts at least one operating parameter of the motor depending on the detected cassette identifier of the pump cassette.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE FIGURES

Exemplary embodiments are described with reference to the accompanying figures, in which.

In the Figures, like reference numbers correspond to like components unless otherwise stated.

DETAILED DESCRIPTION

Applicant has discovered a multi-specialty pump system that can vary the categorical type of pump mechanism based on the pump cassette that is attached to the pump console. The system can include a universal pump console that can accept disposable pump cassettes with tube sets designed for various specialties (e.g., minimally invasive specialties). As such, the pump cassette that is attached to the pump console determines the categorical type of fluid pump mechanism, not the pump console.

The pump cassettes can have equivalent mechanical attachment mechanisms to the pump console, but each cassette can include a different cassette identifier which is recognized by a sensor of the pump console. The pump console can then identify the type of pump cassette that is attached and can adjust at least one operating parameter of the pump console such as the default motor speed, timing, motor direction, and/or the user interface according to the type of pump cassette attached.

Unlike prior pump systems including Stryker's AHTO pump, the type of pump mechanism of the pump system can be determined by the pump cassette and not the pump console, allowing for a modular system that has the ideal pumping mechanism for a given specialty. The pump cassettes attached to the pump console can be interchangeable (i.e., removable and replaceable) with other pump cassettes. For example, for general surgery procedures, a pump cassette with an impeller can be attached to the pump console, thereby making the fluid pump system a centrifugal pump system that can be ideal for high flow rates for laparoscopic irrigation. When a centrifugal pump cassette is attached to the pump console, the pump console can allow the user to pick between flow rates in the laparoscopy mode. In addition, the pump console can drive the motor in a certain (i.e., one) direction. However, for sinuscope cleaning procedures, a pump cassette with a set of peristaltic rollers and flexible tubing can be attached to the pump console, thereby making the fluid pump system a peristaltic pump system allowing for consistent flow rates in a high resistance system. When a peristaltic pump cassette is attached to the pump console, the pump console can allow for consistent flow rates in a high resistance system and for forward and reverse movement of fluid for intraoperative sinuscope cleaning. For example, the pump console can drive the motor forward upon user activation and can temporarily run a reverse cycle when activation is released to remove fluid from the end of an endoscope. In addition, this peristaltic pump system can be designed to work with low torque, DC motors rather than higher torque servo motors. Although only a centrifugal pump cassette and a peristaltic pump cassette were described above, the pump cassettes are not limited to these embodiments and can be other pump cassettes for use in various specialties.

Figure 1:
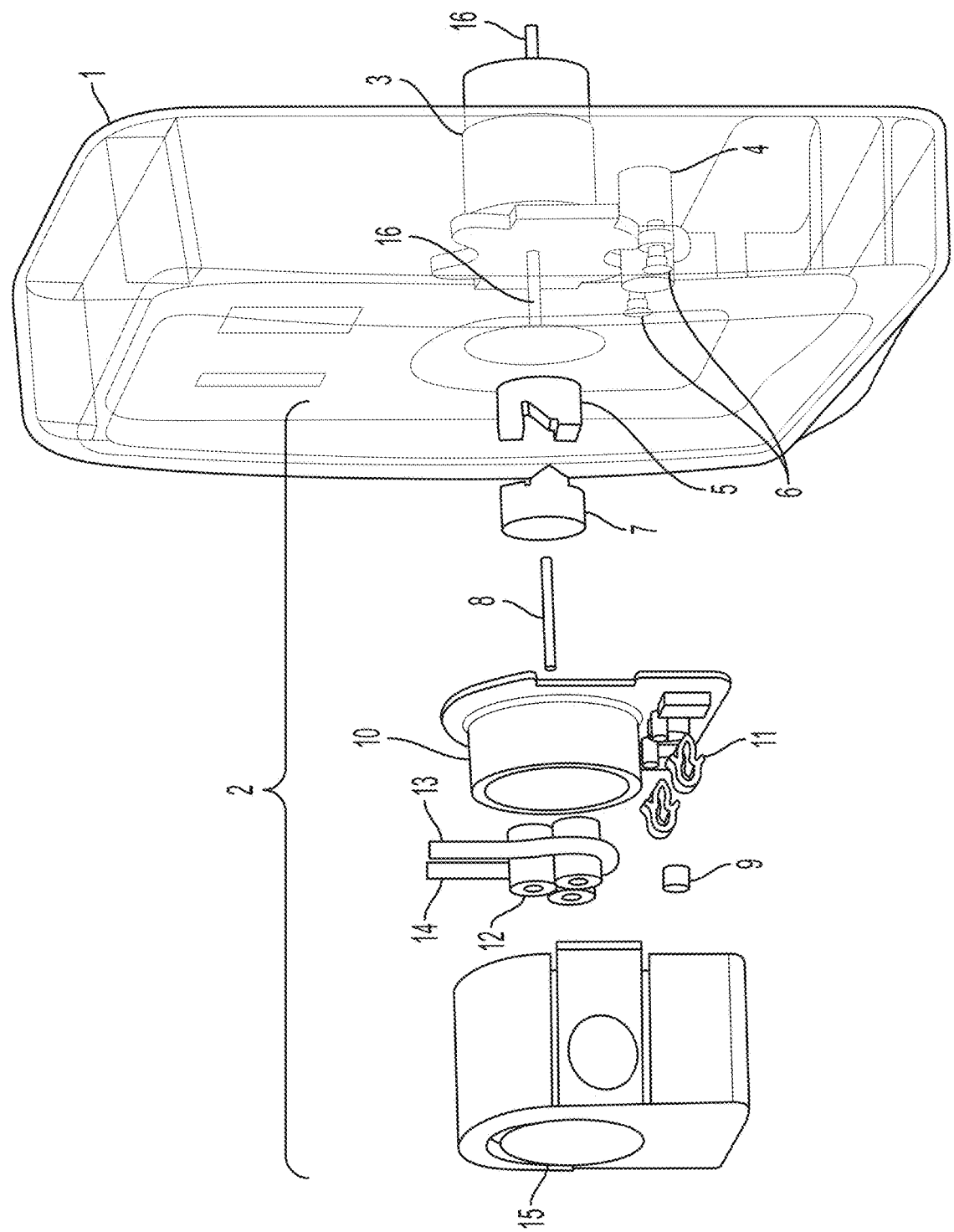
FIG. 1 illustrates an example of an exploded view of a fluid pump system in accordance with some embodiments disclosed herein.

FIG. 1 is an exploded view of a multi-specialty pump system disclosed herein. The pump system can include a pump console 1. The pump console can have a similar form to the existing Stryker AHTO pump which is described in U.S. Pat. No. 8,052,644, which is hereby incorporated by reference in its entirety. In some embodiments, the pump console can have an attachment device on a side of the console. The attachment device can allow the pump console to be attached to various locations in the operating room. In some embodiments, the attachment device allows the pump console to be secured to a pole below a sterile irrigant bag. In some embodiments, the attachment device can be a clamp (e.g., a hand screwed clamp), an adhesive, or Velcro.

Figure 2:
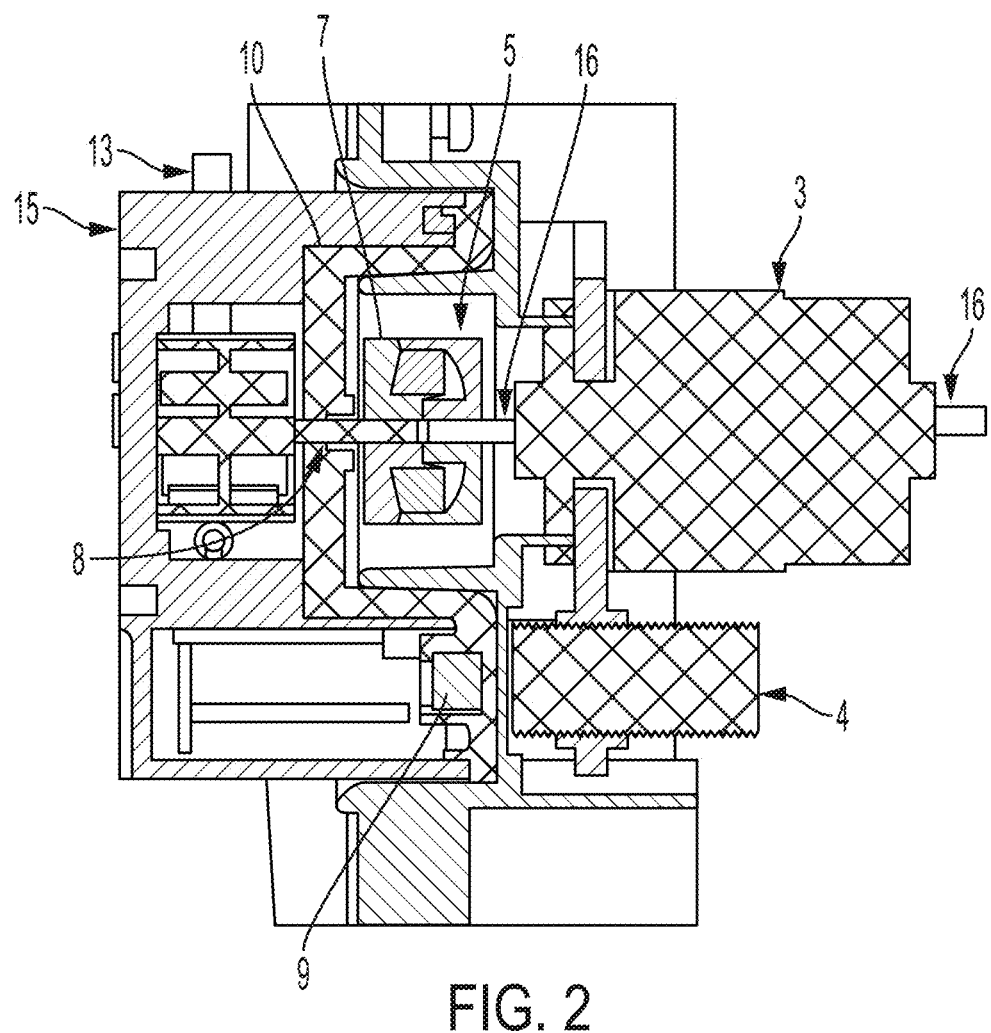
FIG. 2 illustrates an example of a cross sectional view of a pump cassette attached to a pump console in accordance with some embodiments disclosed herein.

The pump console can also include a microcontroller, a motor, a display, a power supply, a battery pack, and/or a sensor to detect the type of pump cassette that is attached. In some embodiments, the pump console includes a reusable battery pack and can therefore be used while plugged into an outlet, or by itself. Accordingly, the pump console can be powered by the battery pack or via a plug in an outlet. Pump console 1 in FIG. 1 illustrates motor 3 and sensor 4. The sensor can be used to determine the type of pump cassette that is attached to the pump console. Specifically, the sensor can detect a cassette identifier of the pump cassette. The cassette identifier is shown in FIG. 1 as cassette identifier 9. In some embodiments, the cassette identifier and the pump console's sensor are aligned such that when the pump cassette is attached to the pump console, the cassette identifier and the pump console's sensor are along the same axis as shown in FIG. 2. In some embodiments, the location of the cassette identifier in the pump cassette can cause the sensor to determine the type of pump cassette that is attached to the pump console.

In some embodiments, the sensor can be a Hall Effect sensor or an RFID sensor. If the sensor is a Hall Effect sensor, the cassette identifier can be a magnet. The Hall Effect sensor can determine the type of pump cassette that is attached based on the strength of the magnet of the pump cassette. As such, different types of pump cassettes can have magnets of different strengths. With a Hall Effect sensor and associated software, the pump console can detect the type of pump cassette that is attached based on the Hall Effect sensor's reading of the magnetic field and the different relative strength of the field at the sensor for each pump cassette. If the sensor is an RFID sensor, the cassette identifier can be an RFID tag. As such, different types of pump cassettes can have different RFID tags. With an RFID sensor and associated software, the pump console can be able to detect the type of pump cassette that is attached based on the RFID sensor's reading of the RFID tag for each pump cassette.

One side of the pump console (e.g., a front side of the pump console) can include a cassette port where the pump cassette can be attached to the pump console. In some embodiments, at least a portion of the pump cassette can be inserted into the cassette port. In some embodiments, the pump cassette can have clips and the pump console can have notches or cutouts for the clips of the pump cassette to snap into place. The pump console can also include a motor coupler fitted or fixed to a motor shaft of the motor. For example, FIG. 1 illustrates motor 3 with motor shaft 16 connected to motor coupler 5.

The pump cassette can also include a cassette coupler fitted or fixed to an end of a cassette shaft. When the pump cassette is attached to the pump console, the motor coupler and the cassette coupler can mate together such that the motor of the pump console can drive the cassette shaft of the pump cassette. FIG. 1 illustrates cassette shaft 8 with cassette coupler 7. The couplers can be how the rotation of the motor in the pump console can directly rotate the cassette shaft which in turn drives the pump mechanism of the pump cassette (e.g., rollers if the pump cassette is a peristaltic pump cassette or an impeller if the pump cassette is a centrifugal pump cassette). When the pump cassette is attached to the pump console, the cassette coupler and the motor coupler can mate together such that the motor of the pump console can drive rotation of the cassette shaft of the pump cassette. FIG. 2 is a cross sectional view of a pump cassette attached to a pump console showing the mating of the motor coupler 5 and the cassette coupler 7. In addition, FIG. 2 also illustrates the alignment of the cassette identifier 9 with the sensor 4 of the pump console when the pump cassette is attached to the pump console.

The pump console can also include at least one electrically conductive contact. FIG. 1 illustrates two electrically conductive contacts 6. The pump cassette can include at least one flexible electrical contact. The at least one flexible electrical contact can mate with the at least one electrically conductive contact of the pump console. The flexibility of the flexible electrical contact may assist with maintaining electrical contact with the conductive contact of the pump console. These contacts can lead to a pump control on each cassette or device attached to the cassette in order to communicate activation of each cassette to the pump console. In some embodiments, the pump control can be mechanically activated (e.g., hand or foot switch), voice activated, or employ another activation type. FIG. 1 illustrates flexible electrical contacts 11 of the pump cassette 2. The electrical contacts can be flexible to enable a more robust contact given the removable nature of the cassette. When the pump cassette is attached to the pump console, the at least one electrically conductive contact of the pump console can be in contact with the at least one flexible electrical contact of the pump cassette. In some embodiments, at least one electrically conductive contact and the at least one flexible electrical contact are aligned such that when the pump cassette is attached to the pump console, the at least one electrically conductive contact and the at least one flexible electrical contact are along the same axis as shown in FIG. 1.

When the at least one electrically conductive contact of the pump console mates with the at least one flexible electrical contact of the pump cassette, any signals from the pump cassette can be sent to the pump console. For example, in some embodiments, the pump cassette can be connected to a pump control. Thus, whenever the user activates the pump control, the at least one flexible electrical contact of the pump cassette can relay to the pump console through the at least one electrically conductive contact that the user has activated the pump control. Once that has been relayed, the motor of the pump console can be activated to drive the cassette shaft. In some embodiments, once the type of cassette has been determined, the actual pumping mechanism can be activated through the contact(s) found on both the pump cassette and the console, when a pump control is activated.

Although examples of controlling the pump console to drive the pump cassettes have been provided that include using a pump control that sends control signals via at least one flexible electrical contact of the pump cassette and at least one electrically conductive contact of the pump console, other types of activation can be used which do not require electrical contacts on the pump cassette and pump console. For example, voice activation of the pump console may not require electrical contacts on the pump cassette and pump console. As another example, the pump console may be communicatively connected to another device (eg. a camera control unit), and a control signal received by the connected device (eg. from a button on an endoscopic camera head) may be relayed to the pump console for activation.

Figure 3A:
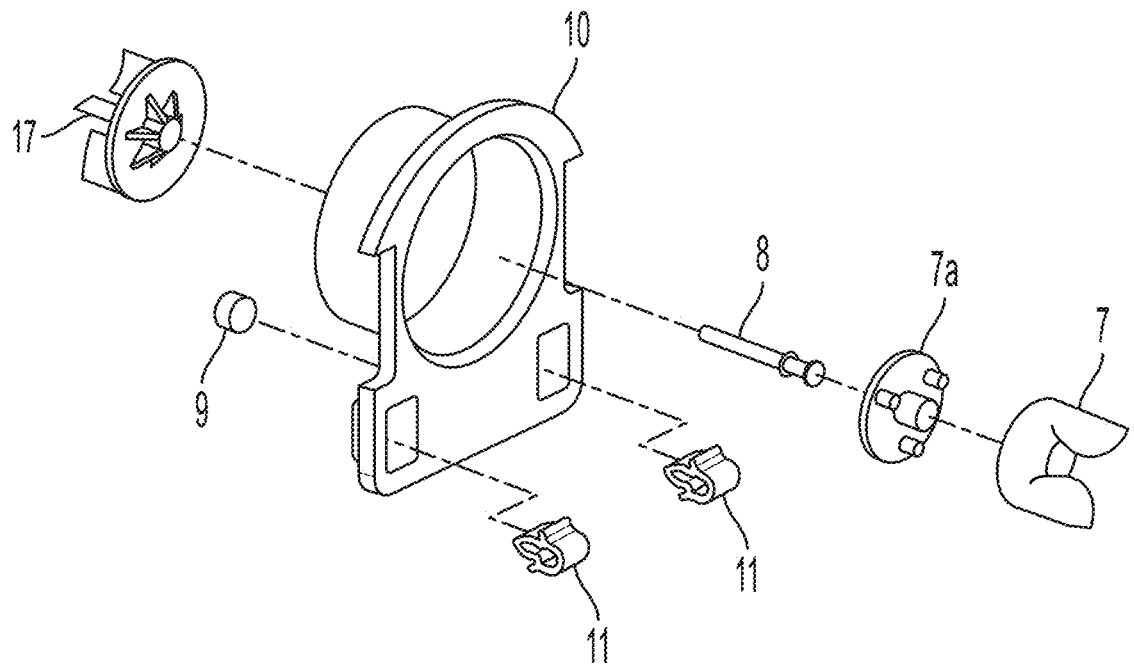
FIG. 3A illustrates an example of an exploded view of a centrifugal pump cassette in accordance with some embodiments disclosed herein.
Figure 3B:
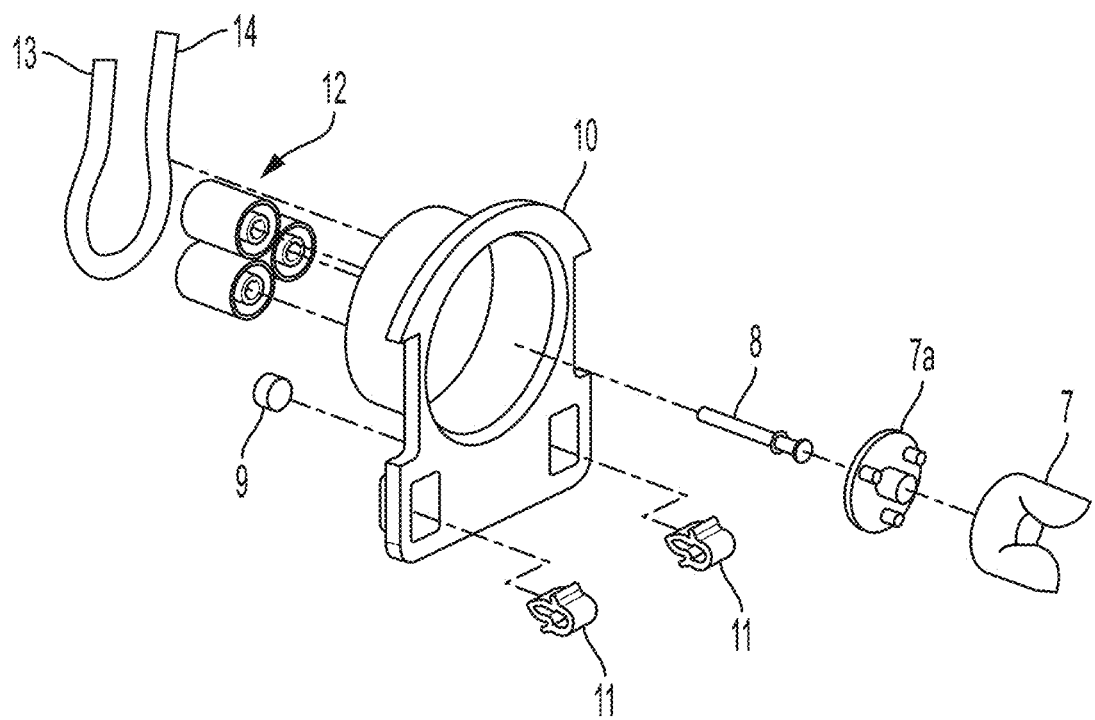
FIG. 3B illustrates an example of an exploded view of a peristaltic pump cassette in accordance with some embodiments disclosed herein.
Figure 4:
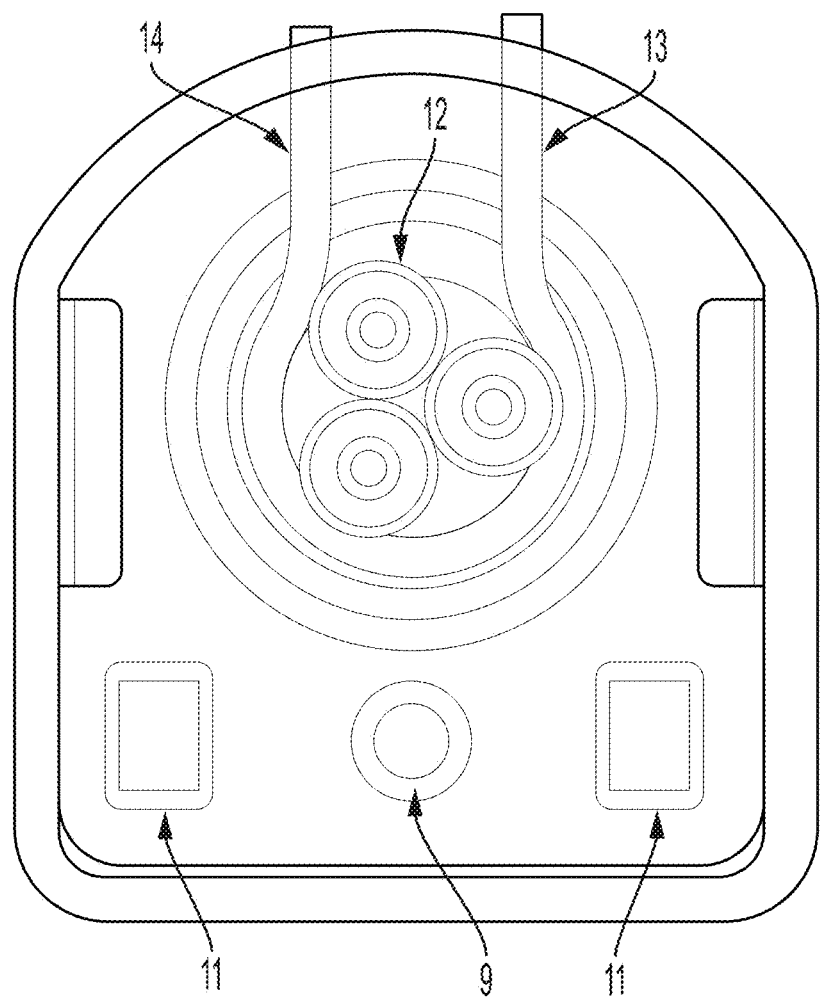
FIG. 4 illustrates a front view of a peristaltic pump cassette with a transparent outer cassette housing in accordance with some embodiments disclosed herein.
Figure 5C:
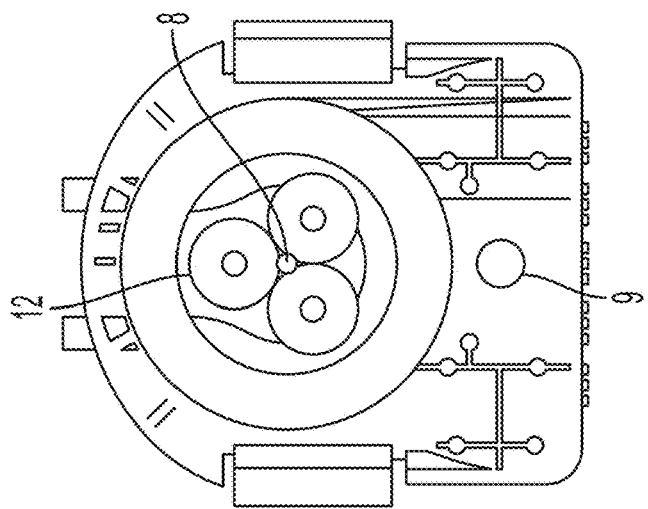
FIG. 5C illustrates a third internal view of a peristaltic pump cassette in accordance with some embodiments disclosed herein.
Figure 5B:
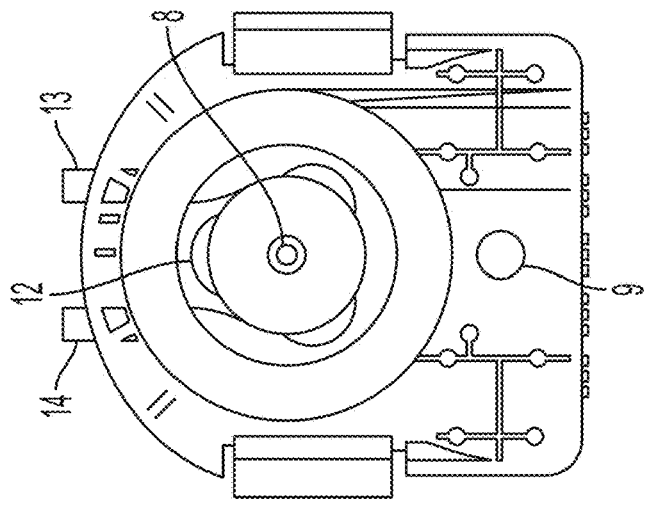
FIG. 5B illustrates a second internal view of a peristaltic pump cassette in accordance with some embodiments disclosed herein.
Figure 5A:
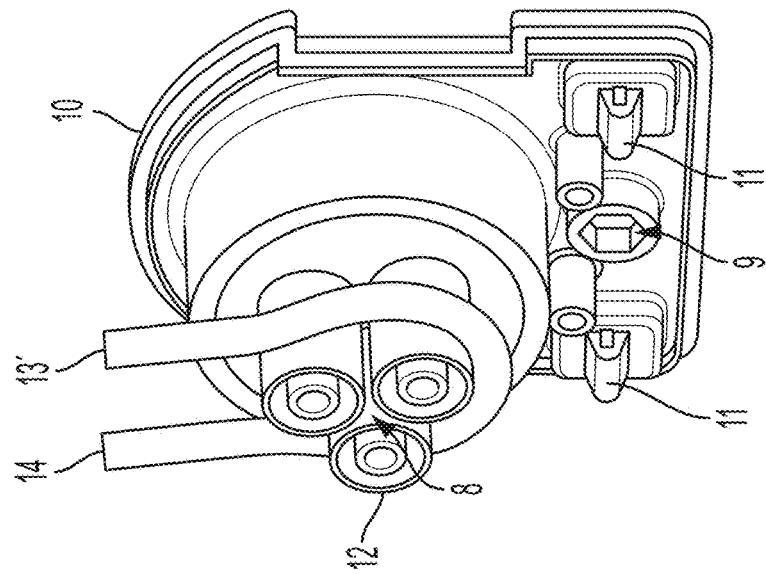
FIG. 5A illustrates a first internal view of a peristaltic pump cassette in accordance with some embodiments disclosed herein.

FIGS. 3A and 3B illustrate examples of exploded views of a centrifugal pump cassette and a peristaltic pump cassette, respectively. As shown in FIG. 3A, the centrifugal pump cassette can include an impeller 17. The impeller can be fixed to an end of the cassette shaft opposite the cassette coupler. In some embodiments, the impeller can rotate at a speed directly proportional to the motor speed, thereby making the pump system a centrifugal pump system. The pump cassette can also include a fluid inlet and a fluid outlet. In some embodiments, the fluid inlet and the fluid outlet are fluidly connected to tubing. The fluid inlet can be fluidly connected to a fluid source such as an irrigation fluid bag.

The fluid outlet can be fluidly connected to a surgical instrument such as an endoscope or irrigator handpiece and suction/irrigation tip. In some embodiments, the centrifugal pump system can deliver high flow rates (e.g., 2-4 L/min) through a relatively large diameter tube to an irrigator handpiece and suction/irrigation tip. For a centrifugal pump cassette, fluid from the fluid source can flow through an internal compartment (e.g., the outer cassette housing) of the pump cassette. The impeller inside the internal compartment can drive fluid out the outlet of the pump cassette through tubing fluidly connected to the pump cassette's fluid outlet at relatively high flow rates (e.g., 2-4 L/min) through a low resistance system In some embodiments, the fluid inlet of the pump cassette can be fluidly connected to tubing with a spike. For example, the fluid source can be a sterile irrigation fluid bag and the tubing spike can be directly spiked into the sterile irrigation fluid bag. The fluid source is not limited to an irrigation fluid bag, but can be a variety of fluid sources such as sterile saline solution bags or sterile water bags. In some embodiments, the spike can be a hollow, tapered spike. The spike can support the tubing which hangs beneath the bag due to the holding force from the spike within the connector. The connector typically can have an elastomer seal that the spike can pierce. Once pierced, the spike can be inserted further. In some embodiments, due to the external taper of the spike, the force required to insert the spike can be higher over the course of the insertion. Once inserted, the tubing can be held in the connector due to friction force. With a tapered spike, the normal force can increase the further the spike is inserted due to the increasing external diameter which consequently increases the friction force. As long as the friction force is larger than the gravitational force on the tubing, the tubing can hang from the bag and not slip out. Alternatively, instead of inserting through an elastomer seal, the connector can also be a short flexible tube. The user can remove some sort of seal and then the spike can be inserted into the tubing end. The same concepts can apply to this type of connector as well. For a peristaltic pump cassette, the tubing with the spike can be fluidly connected to the flexible inlet tubing of the peristaltic pump cassette.

Although not shown in FIG. 3A or 3B, the pump cassette can also include an outer cassette housing. FIG. 1 illustrates outer cassette housing 15. The outer cassette housing of the pump cassette can include the fluid inlet and fluid outlet for the pump cassette. In some embodiments, tubing is connected to the fluid inlet and the fluid outlet of the pump cassette. If the pump cassette is a centrifugal pump cassette, the outer cassette housing can house the impeller. If the pump cassette is a peristaltic pump cassette, the outer cassette housing can house the rollers and flexible tubing.

In some embodiments, the pump cassette can include an inner cassette housing 10. The inner cassette housing can house the cassette coupler as shown in FIG. 2. In some embodiments, the cassette coupler 7 can be connected to a cassette washer 7a which is fixed to an end of the cassette shaft. The cassette shaft can traverse through the inner cassette housing such that the cassette coupler is on one side of the inner cassette housing (i.e., housed inside it) and the impeller (or rollers if a peristaltic pump cassette) is on a side of the inner cassette housing opposite the cassette coupler. In some embodiments, the at least one flexible electrical contact can be connected to the inner cassette housing of the pump cassette. In some embodiments, the cassette identifier can be connected to the inner cassette housing of the pump cassette.

As shown in FIG. 3B, the peristaltic pump cassette can include a plurality of rollers 12. The plurality of rollers can be squeezed between an end of the cassette shaft opposite the cassette coupler and flexible tubing in the pump cassette. FIGS. 1, 2, 3B, 4, and 5A-C all show flexible tubing 13, 14 of the peristaltic pump cassette. The flexible tubing can be fluidly connected to other tubing external to the pump cassette. In some embodiments, flexible tubing 13 is inlet tubing to the peristaltic pump cassette. The inlet tubing can be fluidly connected to a fluid source. In some embodiments, flexible tubing 14 is outlet tubing from the peristaltic pump cassette. The outlet tubing can be fluidly connected to a surgical instrument. In some embodiments, the rigidity of the flexible tubing can prevent back pressure from building in the tubing.

Figure 6:
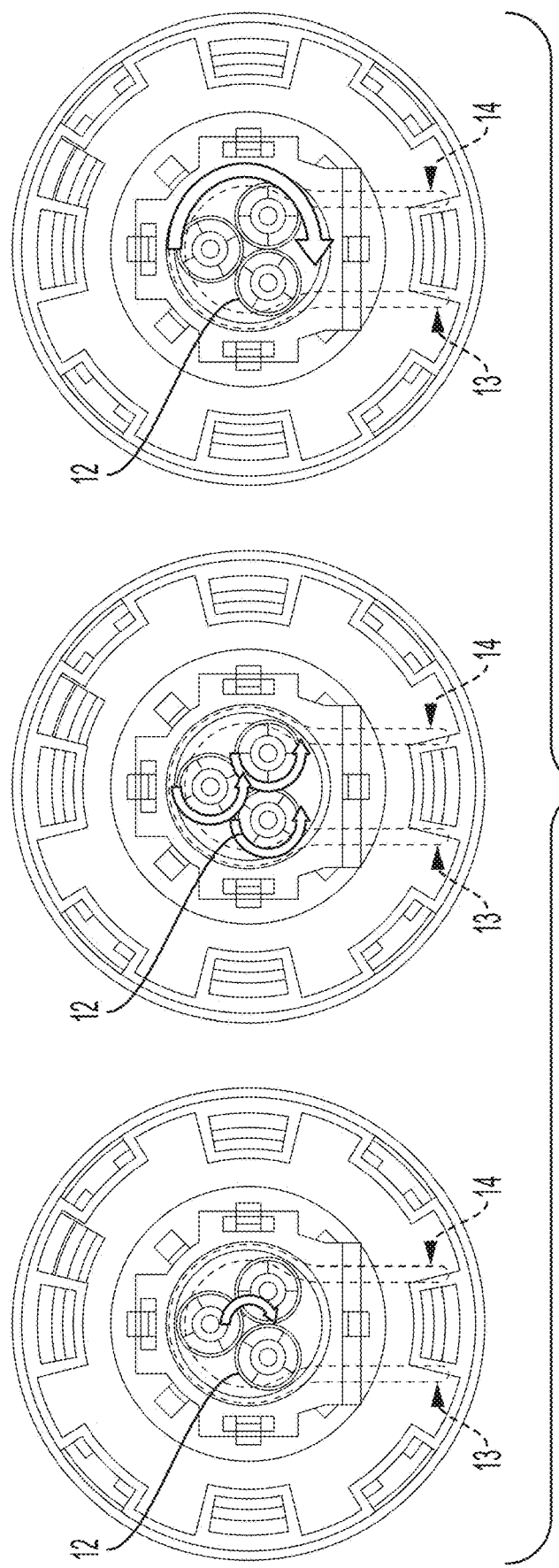
FIG. 6 illustrates a planetary motion diagram for the peristaltic pump used in the peristaltic pump cassette in accordance with some embodiments disclosed herein.

In some embodiments, the outer cassette housing of the pump cassette houses the flexible tubing and the plurality of rollers. The plurality of rollers can press the flexible tubing against the outer cassette housing. In turn, the flexible tubing can also press the plurality of rollers against the cassette shaft at the center between the plurality of rollers. When the motor of the pump console is activated, the rotation of the motor shaft rotates the cassette shaft coupled to the motor shaft. Rotation of the cassette shaft can spin the individual rollers which in turn drives the position of the rollers radially around the cassette shaft. This can allow for a peristaltic pump cassette to be driven by the same low torque DC motor as the centrifugal pump cassette at the cost of high flow rates and maintaining high pressures which may not be needed for a peristaltic pump application. For example, FIG. 6 illustrates a planetary motion diagram for the peristaltic pump used in the pump housing disclosed herein in accordance with some embodiments. FIG. 6 shows that the rollers can be squeezed against the cassette shaft and the flexible tubing, thereby pinching off the flexible tubing. When the motor rotates, the rollers that are pressed against the cassette shaft can rotate individually as well as in the opposite direction of the cassette shaft. Due to the friction and forces pushing the rollers against the flexible tube and the outer cassette housing that houses the rollers and flexible tubing, when the rollers individually rotate, it can cause their position to rotate around the axis of the cassette shaft. Due to the ratio of the sizes between the cassette shaft, rollers, and the outer cassette housing, the rollers can move at a reduced speed from that of the motor, but the motor does not stall from this load. In some embodiments, the pump console can allow for bi-directional movement of fluid by controlling the motor direction. The peristaltic pump cassette attached to the pump console can drive fluid at lower and more consistent flow rates (e.g., 20-60 mL/min) through outlet tubing fluidly connected to the flexible tubing. The outlet tubing can be fluidly connected to an endoscope cleaning sheath or to an internal fluid channel in an endoscope. In such embodiments, the fluid from the pump cassette can intraoperatively clean the end of an endoscope. If the direction of the motor is reversed, fluid can be pulled back in order to remove fluid from the end of the endoscope. In some embodiments, when a user stops the activation of the peristaltic pump cassette, the pump can reverse and pull fluid off the end of the endoscope to provide for a clearer image.

Figure 7B:
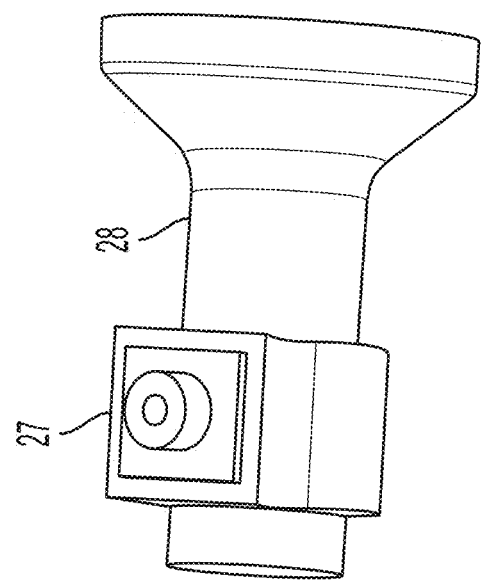
FIG. 7B illustrates a pump control attached to an eyepiece in accordance with some embodiments disclosed herein.
Figure 7A:
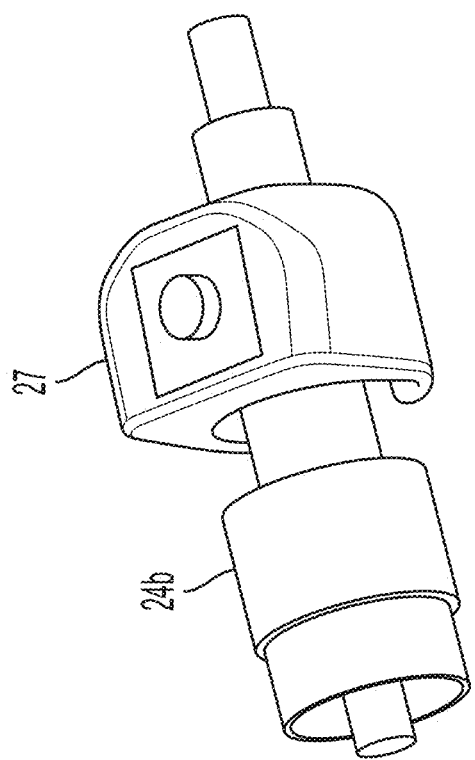
FIG. 7A illustrates a pump control attached to a luer connector in accordance with some embodiments disclosed herein.

As stated above, a pump control can activate the motor of the pump console when the pump cassette is attached to the pump console. In some embodiments, the pump control can be on the pump console such as a switch, button, or icon on the display (i.e., graphical user interface). In some embodiments, the pump control can be a foot-controlled switch. In some embodiments, the pump control can be a hand-controlled switch. As shown in FIGS. 7A and 7B, the pump control can be integrated into mechanical clips that are designed to be attached (e.g., snapped, screwed, hook-and-loop fastened, adhesively applied) onto specific areas on the device such as the shaft of an endoscope sheath or the tubing that connects the pump cassette and the endoscope sheath. In some embodiments, the pump control is attached to a distal end of the tubing in close proximity to the proximal end of an endoscope sheath. FIG. 7A illustrates pump control 27 connected to a luer connector 24B. The luer connector can fluidly connect tubing and an endoscope sheath.

In some embodiments, the pump control can be attached to an endoscope sheath. For example, the pump control can be attached to the shaft of the endoscope sheath or the hub of the endoscope sheath. In some embodiments, the pump control can be attached to the proximal end of the endoscope sheath. In some embodiments, as shown in FIG. 7B, the pump control can be attached to the neck of the eyepiece 28 on the endoscope. The eyepiece can be the most proximal component of the endoscope. The neck of the eyepiece can be the thinner, cylindrical section of the eyepiece before it widens. In some embodiments, the eyepiece is what connects to the coupler on the camera. Putting a hand control at this location can be a possibility as surgeons tend to hold the device in a way that the switch would be easily accessible in this location. In some embodiments, the user can move the location of the pump control.

The pump control can control the pump system (i.e., the pump cassette attached to the pump console). In some embodiments, the pump control can be configured to activate the pump system. In some embodiments, the pump control can be configured to control/regulate the direction of the fluid flow of the pump system. In some embodiments, the pump control can be configured to control/regulate the speed of the pump system. As such, the pump control can be configured to control/regulate the speed and direction of the motor of the pump console, thereby controlling/regulating the speed and direction of the fluid through the pump system.

The pump cassette and/or pump console can be communicatively coupled to the pump control. In some embodiments, the pump console is communicatively coupled to the pump control. As such, the microcontroller of the pump console can be communicatively coupled to the pump control. For example, the pump control can be communicatively coupled to the contact(s) of the pump cassette, the contact(s) of the pump cassette can be communicatively coupled to the contact(s) of the pump console, and the pump console's contact(s) can be communicatively coupled to the microcontroller.

The microcontroller can include a processor, memory, and input/output peripherals that can be used to control the pump system. In some embodiments, the pump console and the pump control are wirelessly communicatively coupled to each other. In some embodiments, the pump console and the pump control are communicatively coupled to each other by wire(s) and contacts.

In some embodiments, the pump console can also include a display. In some embodiments, the display is a graphical user interface. In response to detecting the cassette identifier, the pump console can adjust the display depending on the detected cassette identifier of the pump cassette.

As stated above, the pump console can recognize the type of pump cassette that is attached. Specifically, the pump console's sensor can detect the cassette identifier of the pump cassette. In response to detecting the cassette identifier, the pump console can adjust at least one operating parameter of the motor depending on the detected cassette identifier of the pump cassette. In some embodiments, the at least one parameter of the motor can include motor speed, motor direction, and motor timing. Motor timing can mean a duration for which a given motor speed and direction is maintained during a cleaning cycle according to some embodiments.

When a pump cassette is attached/connected to the pump console, the pump console can recognize the type (e.g., centrifugal, peristaltic, etc.) of pump cassette as previously described. As such, the pump cassette is what drives the type of pump system while the pump console can drive the actual motor. Depending on the pump cassette that is attached, the pump console can determine the program (i.e., what motor speed, motor direction, timing, display settings) to run for the given attached pump cassette. Based on the type of pump cassette that is identified, the pump console can automatically provide feedback to the user regarding the type of pump cassette that is attached as well as provide various options to the user. For example, when a centrifugal pump cassette is attached to the pump console, the pump console can display the mode to the user and provide the option of various flow settings (e.g., low, medium, high). Upon activation of the pump control, the motor can activate at the chosen flow setting to drive fluid through the pump cassette towards a surgical instrument such as a handpiece for laparoscopic suction/irrigation. When activation of the pump control is stopped by the user, the motor can stop.

When a peristaltic pump cassette is attached to the pump console, the display can display the mode to the user (e.g., intraoperative endoscope cleaning). In addition, the pump console can adjust the motor speeds for the peristaltic pump cassette. Upon activation of the pump control, the motor can activate at a predetermined speed to drive fluid through the pump cassette towards a surgical instrument such as an endoscope cleaning sheath to the lens of an endoscope. When activation of the pump control is stopped by the user, the pump console can automatically drive the motor in reverse for a short period of time. This can reverse the flow of fluid and serve to remove any remaining residual fluid from the end of the endoscope and/or remove any backpressure in the tubing.

Figure 8:
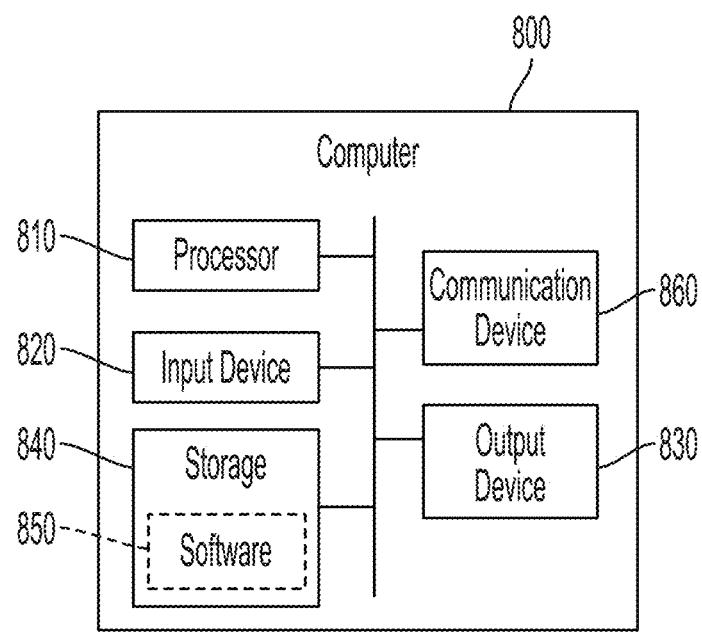
FIG. 8 depicts a computer in accordance with some embodiments disclosed herein.

FIG. 8 illustrates a computer, in accordance with some embodiments. Computer 800 can be a component of a device that can connect to the pump system as described herein. In some embodiments, computer 800 may be configured to execute a method for controlling the pump cassette and pump console of the pump system, as described above.

Computer 800 can be a host computer connected to a network. Computer 800 can be a client computer or a server. As shown in FIG. 8, computer 800 can be any suitable type of microprocessor-based device, such as a personal computer; workstation; server; or handheld computer device, such as a phone or tablet. The computer can include, for example, one or more of processor 810, input device 820, output device 830, storage 840, and communication device 860.

Input device 820 can be any suitable device that provides input, such as a touch screen or monitor, keyboard, mouse, or voice-recognition device. Output device 830 can be any suitable device that provides output, such as a touch screen, monitor, printer, disk drive, or speaker.

Storage 840 can be any suitable device that provides storage, such as an electrical, magnetic, or optical memory, including a RAM, cache, hard drive, CD-ROM drive, tape drive, or removable storage disk. Communication device 860 can include any suitable device capable of transmitting and receiving signals over a network, such as a network interface chip or card. The components of the computer can be connected in any suitable manner, such as via a physical bus or wirelessly. Storage 840 can be a non-transitory computer-readable storage medium comprising one or more programs, which, when executed by one or more processors, such as processor 810, cause the one or more processors to execute methods described herein, such as all or part of the methods described above with respect to controlling the pump system.

Software 850, which can be stored in storage 1040 and executed by processor 1010, can include, for example, the programming that embodies the functionality of the present disclosure (e.g., as embodied in the systems, computers, servers, and/or devices as described above). In some embodiments, software 1050 can be implemented and executed on a combination of servers such as application servers and database servers.

Software 1050 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 840, that can contain or store programming for us by or in connection with an instruction execution system, apparatus, or device.

Software 850 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 800 can implement any operating system suitable for operating on the network. Software 850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example. The above explanation of computer 800 can also apply to the microcontroller of the pump console.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. A fluid pump, comprising:
   a pump console comprising a display, a motor, and a sensor; and
   a pump cassette connected to the pump console comprising a cassette identifier, a pump mechanism, a fluid inlet, and a fluid outlet,
   wherein the sensor detects the cassette identifier, and
   wherein the pump console determines whether the pump mechanism is a centrifugal pump mechanism or a peristaltic pump mechanism depending on the detected cassette identifier of the pump cassette, provides feedback to a user regarding whether the pump mechanism of the pump cassette is a centrifugal pump mechanism or a peristaltic pump mechanism, and adjusts at least one operating parameter of the motor depending on the detected cassette identifier of the pump cassette to drive the pump mechanism of the pump cassette, wherein:
when the pump mechanism of the pump cassette is the centrifugal pump mechanism, the feedback provided to the user comprises displaying, on the display, a centrifugal pump mode and a plurality of centrifugal pump flow setting options, and
when the pump mechanism of the pump cassette is the peristaltic pump mechanism, the feedback provided to the user comprises displaying, on the display, a peristaltic pump mode.

2. The fluid pump of claim 1, wherein the sensor is a Hall Effect sensor and the cassette identifier is a magnet.

3. The fluid pump of claim 1, wherein the sensor is an RFID sensor and the cassette identifier is an RFID tag.

4. The fluid pump of claim 1, wherein the pump cassette is a centrifugal pump cassette comprising an impeller.

5. The fluid pump of claim 1, wherein the pump cassette is a peristaltic pump cassette comprising a plurality of rollers.

6. The fluid pump of claim 1, wherein the at least one operating parameter comprises motor speed, motor direction, and timing.

7. The fluid pump of claim 1, wherein the pump console comprises a motor coupler fixed to a motor shaft of the motor.

8. The fluid pump of claim 7, wherein the pump cassette comprises a cassette coupler fixed to a first end of a cassette shaft and the motor coupler and the cassette coupler mate together such that the motor drives the cassette shaft of the pump cassette.

9. The fluid pump of claim 8, wherein the pump cassette comprises an impeller fixed to a second end of the cassette shaft.

10. The fluid pump of claim 8, wherein the pump cassette comprises a plurality of rollers squeezed between a second end of a cassette shaft and flexible tubing in the pump cassette.

11. The fluid pump of claim 1, wherein the pump console comprises at least one electrically conductive contact.

12. The fluid pump of claim 11, wherein the pump cassette comprises at least one flexible electrical contact, wherein the at least one electrically conductive contact of the pump console is in contact with the at least one flexible electrical contact of the pump cassette.

13. The fluid pump of claim 1, wherein, when the pump mechanism of the pump cassette is the peristaltic pump mechanism:
upon user activation, the pump console drives the motor forward, and
upon user deactivation, the pump console automatically drives the motor in reverse.

14. A pump console comprising a display, a motor, and a sensor, wherein the pump console is configured to:
receive a pump cassette comprising a cassette identifier and a pump mechanism;
detect the cassette identifier of the pump cassette using the sensor;
determine whether the pump mechanism is a centrifugal pump mechanism or a peristaltic pump mechanism depending on the detected cassette identifier of the pump cassette;
provide feedback to a user regarding whether the pump mechanism of the pump cassette is a centrifugal pump mechanism or a peristaltic pump mechanism; and
adjust at least one operating parameter of the motor depending on the detected cassette identifier of the pump cassette to drive the pump mechanism of the pump cassette,
wherein:
when the pump mechanism of the pump cassette is the centrifugal pump mechanism, the feedback provided to the user comprises displaying, on the display, a centrifugal pump mode and a plurality of centrifugal pump flow setting options, and
when the pump mechanism of the pump cassette is the peristaltic pump mechanism, the feedback provided to the user comprises displaying, on the display, a peristaltic pump mode.

15. The pump console of claim 14, wherein the sensor is a Hall Effect sensor and the cassette identifier is a magnet.

16. The pump console of claim 14, wherein the sensor is an RFID sensor and the cassette identifier is an RFID tag.

17. The pump console of claim 14, wherein the pump cassette is a centrifugal pump cassette comprising an impeller.

18. The pump console of claim 14, wherein the pump cassette is a peristaltic pump cassette comprising a plurality of rollers.

19. The pump console of claim 14, wherein the at least one operating parameter comprises motor speed, motor direction, and timing.

20. The pump console of claim 14, further comprising a motor coupler fixed to a motor shaft of the motor.

21. The pump console of claim 20, wherein the pump cassette comprises a cassette coupler fixed to a first end of a cassette shaft and the motor coupler and the cassette coupler mate together when the pump console receives the pump cassette such that the motor drives the cassette shaft of the pump cassette.

22. The pump console of claim 21, wherein the pump cassette comprises an impeller fixed to a second end of the cassette shaft.

23. The pump console of claim 21, wherein the pump cassette comprises a plurality of rollers squeezed between a second end of a cassette shaft and flexible tubing in the pump cassette.

24. The pump console of claim 14, further comprising at least one electrically conductive contact.

25. The pump console of claim 24, wherein the pump cassette comprises at least one flexible electrical contact, wherein the at least one electrically conductive contact of the pump console is in contact with the at least one flexible electrical contact of the pump cassette when the pump console receives the pump cassette.

26. A surgical fluid pump system, comprising:
a pump console comprising a display, a motor, and a sensor;
a pump cassette connected to the pump console comprising a cassette identifier, a pump mechanism, a fluid inlet, and a fluid outlet;
a fluid source fluidly connected to the fluid inlet; and
a surgical instrument fluidly connected to the fluid outlet,
wherein the sensor detects the cassette identifier and the pump console determines whether the pump mechanism is a centrifugal pump mechanism or a peristaltic pump mechanism depending on the detected cassette identifier of the pump cassette, provides feedback to a user regarding whether the pump mechanism of the pump cassette is a centrifugal pump mechanism or a peristaltic pump mechanism, and adjusts at least one operating parameter of the motor depending on the detected cassette identifier of the pump cassette to drive the pump mechanism of the pump cassette, wherein:
when the pump mechanism of the pump cassette is the centrifugal pump mechanism, the feedback provided to the user comprises displaying, on the display, a centrifugal pump mode and a plurality of centrifugal pump flow setting options, and when the pump mechanism of the pump cassette is the peristaltic pump mechanism, the feedback provided to the user comprises displaying, on the display, a peristaltic pump mode.

\* \* \* \* \*